United States Patent [19]

Bondinell et al.

[11] 4,208,430

[45] Jun. 17, 1980

[54] PHARMACEUTICAL COMPOSITIONS AND METHOD OF INHIBITING PHENYLETHANOLAMINE N-METHYLTRANSFERASE

[75] Inventors: William E. Bondinell, Cherry Hill, N.J.; Robert G. Pendleton, Philadelphia, Pa.

[73] Assignee: SmithKline Corporation, Philadelphia, Pa.

[21] Appl. No.: 20,770

[22] Filed: Mar. 15, 1979

[51] Int. Cl.² ........................................... A61K 31/155
[52] U.S. Cl. .................................................. 424/326
[58] Field of Search ......................................... 424/326

[56] References Cited

U.S. PATENT DOCUMENTS

| | | | |
|---|---|---|---|
| 3,845,125 | 10/1974 | Tweit | 424/326 |
| 3,852,353 | 12/1974 | Heaphy | 424/326 |
| 3,868,462 | 2/1975 | Diamond | 424/326 |
| 3,891,204 | 6/1975 | Diamond | 424/326 |
| 3,914,306 | 10/1975 | Douglas et al. | 424/326 |

OTHER PUBLICATIONS

Chem. Abst. 44 8536(c), (1950)–Basil et al.

Primary Examiner—Douglas W. Robinson
Attorney, Agent, or Firm—Joseph A. Marlino; Richard D. Foggio; William H. Edgerton

[57] ABSTRACT

Pharmaceutical compositions and methods of inhibiting phenylethanolamine N-methyltransferase using substituted carbamimidothioic acid phenylalkyl esters.

9 Claims, No Drawings

PHARMACEUTICAL COMPOSITIONS AND METHOD OF INHIBITING PHENYLETHANOLAMINE N-METHYLTRANSFERASE

This invention relates to new pharmaceutical compositions and methods of inhibiting phenylethanolamine N-methyltransferase with substituted carbamimidothioic acid phenylalkyl esters.

Epinephrine is a hormone, synthesized in the adrenal medulla, which is released into the blood stream in response to stress and produces profound physiological changes which serve to prepare the animal to cope with the stressor situation. For example, epinephrine produces anxiety and an increase in cardiac output. These changes are detrimental in individuals with certain disease conditions such as angina pectoris, myocardial infarction and anxiety neuroses.

Phenylethanolamine N-methyltransferase catalyzes the final step in the biosynthesis of epinephrine, that is the transfer of a methyl group from S-adenosylmethionine to norepinephrine to produce epinephrine.

The carbamimidothioic acid ester compounds of the pharmaceutical compositions and methods of this invention inhibit phenylethanolamine N-methyltransferase and thus reduce the formation of epinephrine. They are therefore useful in situations where there is overproduction of epinephrine or where epinephrine production is detrimental.

The compounds which are the active ingredients of the pharmaceutical compositions and methods of this invention are represented by the following formula:

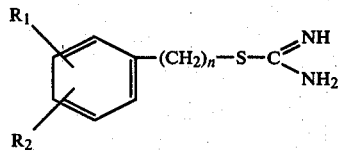

FORMULA 1 in which:
$R_1$ is chloro, bromo, fluoro, iodo, trifluoromethyl or hydrogen, $R_2$ is chloro, bromo, fluoro, iodo, trifluoromethyl, nitro or hydrogen and n is a positive integer from 1 to 3, and pharmaceutically acceptable acid addition salts.

The compounds of this invention are prepared by the following procedure:

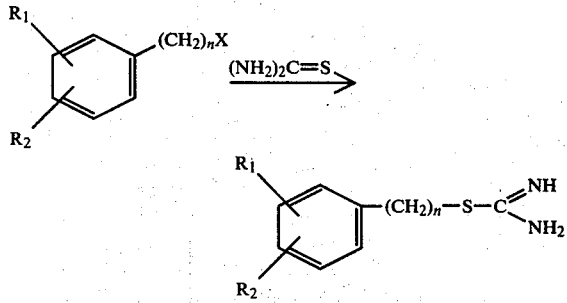

in which
X is bromo or chloro and the terms $R_1$ and $R_2$ are as defined above.

According to the above procedure the substituted carbamimidothioic acid phenylalkyl esters are prepared by reacting the appropriate phenylalkyl halide with thiourea in an organic solvent. The phenylalkyl halide starting materials are generally known or can be prepared from readily available starting materials.

Pharmaceutically acceptable acid addition salts of the compounds of Formula 1 are formed with organic and inorganic acids by methods known to the art. The base is reacted with an organic or inorganic acid in aqueous miscible solvent, such as acetone or ethanol, with isolation of the salt by concentration and cooling or in aqueous immisicible solvent, such as ethyl ether or chloroform, with the desired salt separating directly. Exemplary of the salts which are included in this invention are maleate, fumarate, benzoate, ascorbate, pamoate, succinate, bismethylenesalicylate, methanesulfonate, ethanedisulfonate, benzenesulfonate, acetate, propionate, tartrate, salicylate, citrate, gluconate, lactate, malate, mandelate, cinnamate citraconate, aminobenzoate, glutamate, theophylline acetates, hydrochloride, hydrobromide, sulfate, cyclohexylsulfamate, phosphate and nitrate salts.

The compounds of this invention are known. For example, the 3,4-dichlorobenzyl ester is disclosed in C. A. 58:3340c, the nitro esters are disclosed in C. A. 55:8362a, the trifluoromethyl ester in C. A. 68:77896h, and the monochloro esters in C. A. 44:8536d.

The basic activity of the active ingredients of this invention is demonstrated by inhibition of phenylethanolamine N-methyltransferase in vitro by the assay procedure described by Pendleton and Snow, Molecular Pharmacology, 9:718-725, 1973, at various compound concentrations. For example, at a concentration of $10^{-4}$ a preferred active ingredient of this invention carbamimidothioic acid 3,4-dichlorophenethyl ester inhibits phenylethanolamine N-methyltransferase by 100% and at a concentration of $10^{-6}$ by 75%.

The pharmaceutical compositions of this invention to inhibit phenylethanolamine N-methyltransferase comprise a pharmaceutical carrier and, as the active ingredient, a carbamimidothioic acid ester of Formula 1. The active ingredient will be present in the compositions of this invention in an effective amount to inhibit phenylethanolamine N-methyltransferase.

Preferably, the compositions of this invention contain the active ingredient of Formula 1 in an amount of from about 50 mg. to about 1000 mg., advantageously from about 100 mg. to about 500 mg., per dosage unit.

The pharmaceutical carrier may be for example a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example, the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of inhibiting phenylethanolamine N-methyltransferase, according to this invention, comprises administering to an animal in an amount sufficient to inhibit phenylethanolamine N-methyltransferase a carbamimidothioic acid ester compound of Formula 1.

Preferably the compounds of Formula 1 are administered in conventional dosage unit forms prepared by combining an appropriate dose of the compound with standard pharmaceutical carriers.

Preferably the active ingredient of Formula 1 will be administered in a daily dosage regimen of from about 100 mg. to about 2000 mg., most preferably from about 200 mg. to about 1000 mg. Advantageously, equal doses will be administered preferably two to three times per day. When the administration is carried out as described above, inhibition of phenylethanolamine N-methyltransferase is produced.

The route of administration of the pharmaceutical compositions of this invention and in accordance with the methods of this invention is internal, either parenteral or preferably oral, in an amount to produce the desired biological activity.

The following examples are not limiting but are illustrative of this invention.

EXAMPLE 1

2,3-Dichlorotoluene (8.05 g., 0.05 mol.) dissolved in 150 ml. of carbon tetrachloride containing N-bromosuccinimide (8.9 g., 0.05 mol.) was heated to reflux and irradiated with a 275-watt sunlamp for two hours. The mixture was cooled, filtered and evaporated to give α-bromo-2,3-dichlorotoluene. The α-bromo-2,3-dichlorotoluene (2.4 g., 0.01 mol.) and thiourea (0.38 g., 0.005 mol.) were dissolved in 25 ml. of ethanol and refluxed for about sixteen hours. The mixture was cooled, concentrated, treated with ether, filtered and the filter cake recrystallized from water to give carbamimidothioic acid 2,3-dichlorobenzyl ester, m.p. 238°–243° C. (dec.).

EXAMPLE 2

3,4-Dichlorophenethyl chloride (0.8 g., 0.004 mol.) and thiourea (0.26 g., 0.0035 mol.) in 25 ml. of ethanol were refluxed for two days. The mixture was concentrated and the residue treated with ether to give a solid which was recrystallized from acetone to yield carbamimidothioic acid 3,4-dichlorophenethyl ester, m.p. 135°–139° C.

EXAMPLE 3

Following the procedure of Example 1 the following substituted compounds:
3,4-dichlorophenylpropyl chloride
3,4-bis(trifluoromethyl)toluene
4-nitrobenzyl chloride
2-phenylethyl chloride
2-(4-chlorophenyl)ethyl chloride
4-trifluoromethylbenzyl bromide
4-chloro-3-nitrobenzyl chloride
are used as starting materials to give the following products respectively:
Carbamimidothioic acid 3,4-dichloro phenylpropyl ester
Carbamimidothioic acid 3,4-(bistrifluoromethyl)benzyl ester
Carbamimidothioic acid (4-nitro)benzyl ester
Carbamimidothioic acid 2-phenylethyl ester
Carbamimidothioic acid-2-(4-chlorophenyl)ethyl ester
Carbamimidothioic acid-4-trifluoromethylbenzyl ester
Carbamimidothioic acid-4-chloro-3-nitrobenzyl ester

EXAMPLE 4

| Ingredient | Mg./Capsule |
|---|---|
| Carbamimidothioic Acid 3,4-Dichlorophenethyl Ester | 150 mg. |
| Lactose | 150 mg. |

The above ingredients are mixed and filled into a hard gelatin capsule.

One capsule is given three times a day.

EXAMPLE 5

| Ingredients | Mg./Tablet |
|---|---|
| Carbamimidothioic Acid 2,3-Dichlorobenzyl Ester | 50 mg. |
| Calcium Sulfate dihydrate | 150 mg. |
| Sucrose | 25 mg. |
| Starch | 15 mg. |
| Talc | 5 mg. |
| Stearic Acid | 3 mg. |

The sucrose, calcium sulfate and thioic acid ester are thoroughly mixed and granulated with hot 10% gelatin solution. The wetted mass is passed through a No. 6 mesh screen directly onto drying trays. The granules are dried at 120° C. and passed through a No. 20 mesh screen, mixed with starch, talc and stearic acid and compressed into tablets.

Two tablets are administered three times a day.

What is claimed is:

1. A method of inhibiting phenylethanolamine N-methyltransferase which comprises internally administering to an animal in need of said treatment an amount sufficient to produce said inhibition a chemical compound of the formula:

$$\text{R}_1\text{-C}_6\text{H}_3(\text{R}_2)-(\text{CH}_2)_n-\text{S}-\text{C}(=\text{NH})\text{NH}_2$$

in which:
R$_1$ is chloro, bromo, fluoro, iodo, trifluoromethyl, or hydrogen; R$_2$ is chloro, bromo, fluoro, iodo, trifluoromethyl, nitro, or hydrogen; and n is a positive integer from 1 to 3, or a pharmaceutically acceptable acid addition salt thereof.

2. A method of inhibiting phenylethanolamine N-methyltransferase which comprises internally administering to animals in need of said inhibition a dosage unit of from about 50 mg. to about 1000 mg. of a compound as defined in claim 1.

3. The method of claim 1 in which R$_1$ is hydrogen.
4. The method of claim 3 in which n=2.
5. The method of claim 4 in which R$_2$ is 4-nitro.
6. The method of claim 4 in which R$_2$ is hydrogen.
7. The method of claim 3 in which R$_2$ is 4-trifluoromethyl and n=1.
8. The method of claim 1 in which R$_1$ and R$_2$ are 3,4-dichloro and n=2.
9. The method of claim 1 in which R$_1$ and R$_2$ are 2,3-dichloro and n=1.